(12) United States Patent
Ramachandran et al.

(10) Patent No.: US 9,593,943 B2
(45) Date of Patent: Mar. 14, 2017

(54) CLAMP MECHANISM FOR CLAMPING AN OPTICAL SHAPE SENSING FIBER

(71) Applicant: KONINKLIJKE PHILIPS N.V., Eindhoven (NL)

(72) Inventors: Bharat Ramachandran, Morganville, NJ (US); Martinus Bernardus Van Der Mark, Best (NL); Karen Irene Trovato, Putnam Valley, NY (US); Cornelius Antonius Nicolaas Maria Van Der Vleuten, Liempde (NL); David Paul Noonan, New York, NY (US); Molly Lara Flexman, Melrose, MA (US); Jeroen Jan Lambertus Horikx, Weert (NL); Anna Hendrika Van Dusschoten, Eindhoven (NL); Elbert Gerjan Van Putten, S-Hertogenbosch (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/025,403

(22) PCT Filed: Sep. 30, 2014

(86) PCT No.: PCT/EP2014/070982
§ 371 (c)(1),
(2) Date: Mar. 28, 2016

(87) PCT Pub. No.: WO2015/049256
PCT Pub. Date: Apr. 9, 2015

(65) Prior Publication Data
US 2016/0231104 A1 Aug. 11, 2016

(30) Foreign Application Priority Data

Oct. 2, 2013 (EP) ..................................... 13187029

(51) Int. Cl.
*G02B 6/00* (2006.01)
*G01B 11/24* (2006.01)
(Continued)

(52) U.S. Cl.
CPC .............. *G01B 11/24* (2013.01); *A61B 34/20* (2016.02); *G01B 11/16* (2013.01); *G01D 5/353* (2013.01);
(Continued)

(58) Field of Classification Search
CPC .. G02B 6/3624; G02B 6/3632; G02B 6/3636; G02B 6/4439; G01B 11/16;
(Continued)

(56) References Cited

U.S. PATENT DOCUMENTS 4,088,386 A * 5/1978 Hawk ................. G02B 6/3809
385/59
4,201,444 A 5/1980 Arnold et al.
(Continued)

FOREIGN PATENT DOCUMENTS

CN 102401939 A 4/2012
FR 2446496 A1 8/1980
KR 20130024012 A 3/2013

*Primary Examiner* — AKm Enayet Ullah
*Assistant Examiner* — Michael Mooney

(57) ABSTRACT

A clamp mechanism for fixation of an optical fiber (OSF) with optical shape sensing properties arranged for Optical Shape Sensing. A fixing element preferably with a circular cross section serves to engage with the optical fiber (OSF), and together with an additional fixing arrangement with a straight longitudinal portion arranged for engaging with the associated optical fiber (OSF), a fixation of a section of the optical fiber (OSF) is provided with the optical fiber (OSF) in a straight position. In some embodiments, the clamp mechanism can be implemented by three straight rods (R1, R2, R3) with circular cross section, e.g. with the same diameter being a factor of such as 6.46 times a diameter of (Continued)

the optical fiber (OSF). Hereby an effective fixation and straightening of the optical fiber (OSF) without disturbing strain can be obtained with a clamp mechanism which is easy to assemble and disassemble in practical applications e.g. when used as a launch fixture, and with the optical fiber (OSF) incorporated in a medical device.

10 Claims, 10 Drawing Sheets

(51) Int. Cl.
*G01N 21/00* (2006.01)
*G02B 6/44* (2006.01)
*G01M 11/00* (2006.01)
*G01D 5/353* (2006.01)
*G01B 11/16* (2006.01)
*G02B 6/36* (2006.01)

(52) U.S. Cl.
CPC ............ *G01M 11/30* (2013.01); *G02B 6/4439* (2013.01); *A61B 2034/2061* (2016.02); *G02B 6/3624* (2013.01); *G02B 6/3632* (2013.01); *G02B 6/3636* (2013.01)

(58) Field of Classification Search
CPC . G01B 11/24; A61B 34/20; A61B 2034/2061; G01M 11/30; G01D 5/353
USPC ............ 385/12, 13, 82, 123–128, 136, 137; 356/73.1, 477, 601; 600/424
See application file for complete search history.

(56) References Cited

U.S. PATENT DOCUMENTS

| | | |
|---|---|---|
| 4,490,007 A | 12/1984 | Murata |
| 8,050,523 B2 | 11/2011 | Younge et al. |
| 2009/0099551 A1 | 4/2009 | Tung et al. |
| 2012/0266442 A1 | 10/2012 | Rogers et al. |

\* cited by examiner

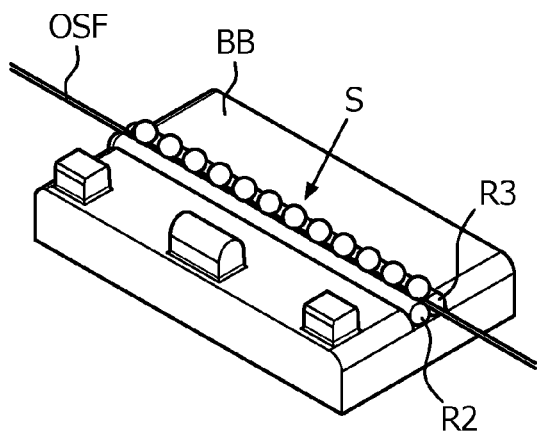 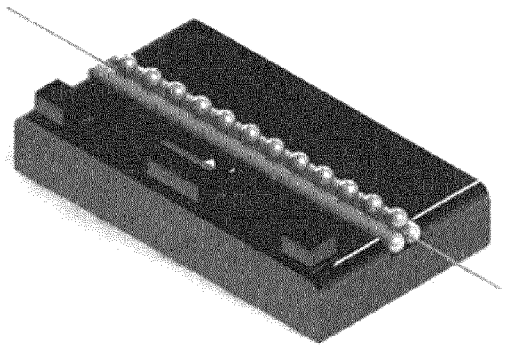
FIG. 16a         FIG. 16b
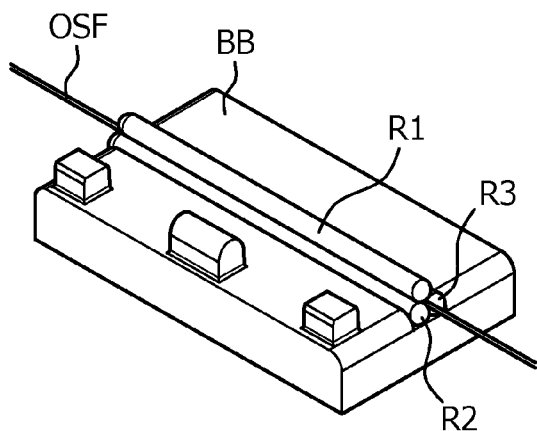 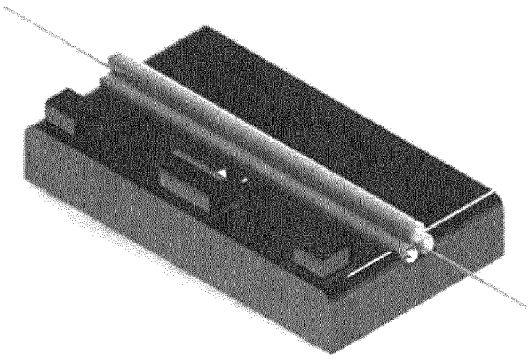
FIG. 17a         FIG. 17b

CLAMP MECHANISM FOR CLAMPING AN OPTICAL SHAPE SENSING FIBER

CROSS-REFERENCE TO PRIOR APPLICATIONS

This application is the U.S. National Phase application under 35 U.S.C. §371 of International Application Serial No. PCT/EP2014/070982, filed on Sep. 30, 2014, which claims the benefit of European Patent Application Serial No. 13187029.7, filed on Oct. 2, 2013. These applications are hereby incorporated by reference herein.

FIELD OF THE INVENTION

The present invention relates to the field of optical shape sensing (OSS), especially the invention provides a clamp mechanism for clamping an OSS fiber in an OSS device, e.g. for clamping in a launch fixture or for other clamping purposes, e.g. for registration purposes.

BACKGROUND OF THE INVENTION

In optical shape sensing (OSS), the distributed backscattering of light over the entire length of a multi-core optical fiber is measured. The backscattering may come from the naturally occurring Rayleigh scattering or from Bragg gratings written into the fiber (FBGs, Fiber Bragg Gratings). With use of optical interferometric methods, the distributed strain pattern over the entire length and diameter of the optical fiber is interrogated and from that it is possible to reconstruct a 3D shape of the optical fiber, which is useful e.g. when the optical fiber is incorporated in an elongated device such as a medical catheter or guide wire. This requires that the optical fiber has a straight section, called the launch region, with known orientation and position in space as a starting point for a reconstruction of the shape of the optical fiber. This may be achieved by sticky tape or by gluing the starting point on a microscope object side, or by sliding a few centimeters of straight, tightly fitting capillary over the optical fiber. In case the optical fiber is used for tracking position and shape of a medical instrument, such as a guide wire or a catheter, the optical fiber is integrated into the instrument. Integration puts boundary conditions on the manufacturability, placement and stability of the launch region.

Typically, a so-called launch fixture is used to clamp the optical fiber properly as well as to keep track of the position and orientation of the starting point. Small deviations in angle or straightness in the launch region may lead to rather large deviations 1 or 2 meters away from the launch region. E.g. a deviation of 10 micron over 2 cm corresponds to a mismatch of 1 mm at 2 meter, and this example is typical for what is normally considered as just allowable, e.g. for medical application of OSS. It should be noted that clamping of the optical fiber has to be done with care in order to avoid high pressure or uneven distribution of pressure on the launch region because those pressures will change the strain reading of that region compared to the low strain reference values measured originally measured for calibration purposes on the fiber when straightened.

Present launch fixtures are either unpractical, or they simply do not provide the required accuracy, since they are not able to prevent the optical fiber from translating or twisting, while maintaining uniform strain across the launch region. Certain ways of gluing induce creep or are unstable over time, in particular if the instrument, e.g. a catheter or a guide wire, in which the optical fiber is integrated, is operated and stresses are transported to the launch fixture. Sticky tape or Salol are examples of how to make a removable fixation, but both fail to provide the desired stability. Also, tightly fitting of capillary tubing placed around the fiber must be slid over the whole fiber and cannot be applied once the fiber has been terminated, connectorized or integrated in a medical device. Furthermore, it is difficult to assure that the fiber is stress free inside the tube, or that it is fitting correctly. This appears to be true in particular if glue is used to fixate the position and rotation of the fiber.

Thus, none of the existing fixing methods can comply with all of:
1) provide a straight launch region (better than 10 micron over 20 mm for 1 mm tip accuracy),
2) be stable over time and temperature changes,
3) allow easy removal of the optical fiber, and
4) provide no or limited strain exerted on the launch region.

SUMMARY OF THE INVENTION

Following the above description of background information, it would be advantageous to provide a clamp mechanism for an optical fiber arranged for OSS, which is preferably capable of complying with all of the restrictions:
1) provide a straight launch region (better than 10 micron over 20 mm for 1 mm tip accuracy),
2) be stable over time and temperature changes,
3) allow easy removal of the optical fiber, and
4) provide no or limited strain exerted on the launch region.

Further, it may be preferred that the clamp mechanism can be easily manufactured, and that it is easy to use for practical applications where an OSS optical fiber is integrated in a device or instrument, e.g. a medical instrument.

In a first aspect, the invention provides a clamp mechanism arranged for fixation of an associated optical fiber comprising optical shape sensing properties and configured for being repeatedly assembled and take apart around the optical fiber, the clamp mechanism comprising
a fixing element comprising a straight rod with a circular cross section, which is arranged for engaging with the associated optical fiber, and
an additional fixing arrangement comprising two straight rods with circular cross sections and a straight longitudinal portion arranged for engaging with the associated optical fiber, and a base block with an opening section arranged for receiving the two straight rods of the additional fixation arrangement and the straight rod of the fixation element, whereby the straight rod of the fixing element is arranged, together with the two straight rods of the additional fixing arrangement, to form an opening arranged for fixation of a section of the associated optical fiber in a straight position. Such clamp mechanism is advantageous, since it allows manufacturing of a rather simple clamp mechanism which can clamp or fix an optical fiber for OSS in general, e.g. for registration at a given position in space. However, the clamp mechanism can also function as a launch fixture, since it can comply with all of the above-mentioned restrictions 1)-4). The clamp mechanism is even possible to implement with rather simple single elements which are easy to assemble around the optical fiber (and be taken apart again), and which are based on simple geometrical shapes which can easily be manufactured, e.g. in metal, with a high accuracy and with a size precisely matching a given size of optical fiber for optimal clamping. The invention is based on the insight that the fixing element and the additional fixing arrangement can be constituted by elements with simple shapes and still provide the required accuracy with respect to straightness and freedom of stress and twisting of the optical fiber without the need for gluing etc.

Further, the clamp mechanism is highly suited for manufacturing in versions shaped to fit a specific OSS device or instrument, e.g. a launch fixture. This allows fast mounting of the launch fixture to an OSS device or instrument in practical use.

By 'engaging with the optical fiber' is understood direct or indirect engagement, since e.g. a thin cover or coating may be used to cover the single optical fibers of a multi-core optical fiber, and still it is to be understood that in such case, the fixing element and the additional fixing arrangement are not in direct contact with the optical fiber(s) as such, but rather in direct contact with the thin cover which is to be understood as being part of the 'optical fiber'. Thus 'optical fiber with optical shape sensing properties' is understood to cover an appropriate optical fiber with a coating or cover.

In the following, some principal embodiments will be defined.

In some embodiments, the fixing element may be one single element only, while the additional fixing arrangement may include two and more single elements. Such single element constituting the fixing element may especially be a monolithic element, even more specifically it may be a monolithic element with a cross sectional area. However, in other embodiments, the fixing element comprises a plurality of single elements, especially it may comprise a plurality of spherical elements.

A cross sectional area of the fixing element in the straight longitudinal portion may be larger than a cross sectional area of the associated optical fiber. In some embodiments with circular cross section, it may be preferred that the diameter of a cross section of the fixing element is a factor of 5-8, such as a factor of 6-7, such as a factor of 6.3-6.6, times a cross sectional diameter of the optical fiber (including any optional coating or covering).

The additional fixing arrangement may comprise a a monolithic base block with an opening section arranged for receiving further single elements forming the additional fixing arrangement and/or single elements forming the fixing element.

Additionally, the straight rod of the fixing element, and the two straight rods of the additional fixing arrangement may all have circular cross sections with equal or substantially equal diameters. The cross sectional diameter of the straight rod of the fixing element may be selected to be slightly smaller than the cross sectional diameter of the two straight rods of the additional fixing arrangement. It is to be understood that the cross sectional area of the rods are preferably matched with the cross sectional area of the optical fiber in order to obtain a fixation effect without squeezing the optical fiber. The selection of diameter will be described later. By tuning the size of only one of the rods, it is possible in one case to let the optical fiber slide, but still keep it straight, and in another case to clamp the optical fiber tight enough to keep both its axial and rotational position fixed.

Such 3-rod embodiments mentioned above can be easily manufactured, e.g. in lengths of such as 10-50 mm and such rods can form the basis for a clamp mechanism which can serve as a launch fixture. Additionally, the clamp mechanism may comprise an element or member arranged to press the three rods together. E.g. a base block with an opening may serve to accommodate two of the rods with a tight fit, i.e. with a width of exactly two times the diameter of the two rods, and with an element fixed to the base block, and with a member arranged to press the top rod against the two rods positioned in the opening section of the base block. E.g. this may be obtained with a screw and thread arrangement, where the thread is provided in the base block.

In some versions of the 3-rod embodiments, at least one of the straight rods has a rounded end portion. Especially, all of the three rods have rounded end portions, in one end or in both ends. This is advantageous with respect to avoid pinching of the optical fiber at the ends of the rods.

In some embodiments, at least a part of the fixing element and a part of the additional fixing arrangement have magnetic properties, so as to magnetically attract each other in an assembled state of the clamp mechanism. Hereby, magnetic forces are used to apply a force serving to press the fixing element and the additional fixing arrangement together, and thus serve to fix the optical fiber placed in between. E.g. in 3-rod embodiments, two of the rods may be formed by magnetic materials, or may be magnetized.

The fixing element may comprise a spherical body. In the above-mentioned 3-rod embodiments, the straight rod of the fixing element may be replaced by a sphere, or a number of spheres, serving to engage with the additional fixing arrangement instead of a rod. Especially, the additional fixing arrangement may be, as described above, i.e. with two straight rods, e.g. placed in an opening section of a base block. In a special embodiment, the fixing element is constituted by one single spherical body, while the additional fixing arrangement comprises two spherical bodies, e.g. all three spheres may be of equal diameter. Embodiments with a spherical body may not provide the same requirement to straightening of the optical fiber as a rod as required for a launch fixture, however for some applications, e.g. clamping for registration purposes, the fixing effect may suffice. In particular, from three spheres a well-defined hole can be created through which the fiber may slide, thus representing a movable point in space. Further, if the fixing element comprises a plurality of spherical body elements, e.g. 2-10 spherical elements, in combination with an additional fixing arrangement comprising two straight rods, a sufficient straightening of the optical fiber may obtained.

The additional fixing arrangement may comprise a body with a straight groove with an opening angle, wherein the straight groove is arranged to accommodate a section of the associated optical fiber, and to fix the associated optical fiber in a straight position in cooperation with the fixing element. Such embodiment may be combined with a fixing element in the form of a straight rod, or in the form of one or more spherical bodies. It is to be understood that the opening angle of the groove should be selected to fit to the size and shape of the fixing element, and the size of the optical fiber, in order to obtain the desired clamping effect over the desired length of the optical fiber.

An end portion of the fixing element, and an end portion of the additional fixing arrangement, may be shaped for holding an end portion of an associated device in which the associated optical fiber is incorporated. This is advantageous, since it is possible to design the fixing element and the additional fixing arrangement to match the shape of the tip of e.g. a medical catheter, guide wire, or another device, which provides an easy fit for such device to the clamp mechanism, if the clamp mechanism forms part of a launch fixture. Thus, such embodiments provide e.g. a practical feature for mounting of an OSS device to a launch fixture that can save time for practical application.

This matching to a device in which the optical fiber is incorporated can still be provided with rather geometrically simple means, where only an end part is modified in a simple manner. Especially, in case of the above mentioned 3-rod embodiments, end portions of all three rods may have a smaller diameter than the remaining longitudinal extension of the rods serving for fixing the optical fiber. This smaller diameter of the three rods is preferably selected so as to form an opening which matches the shape of a tip of an associated device, such that it serves to hold the associated device in position, when the optical fiber of the device is clamped in the clamp mechanism. The transition between the main part of the rods and the end part with a smaller diameter, may be provided by a tapering region forming a gradual change of diameter over a certain length, however this tapering region may be of zero length.

The associated optical fiber may especially have optical shape sensing properties comprising backscattering properties used for optical shape sensing. Especially, the optical fiber may comprise at least one of the properties: Rayleigh scattering and fiber Bragg gratings. Especially, the optical fiber may be a multi-core optical fiber with a plurality of single-mode cores. More specifically, the optical fiber may comprise a coating or cover.

In a second aspect, the invention provides an optical shape sensing system comprising:
an elongated device comprising an optical fiber comprising optical shape sensing properties,
a clamp mechanism according to the first aspect, and
an optical console system arranged for interrogating the optical fiber, e.g. interrogating a distribution of strain in the optical fiber, and to accordingly determine a measure of a three-dimensional shape of at least a part of the optical fiber.

The clamp mechanism may be arranged for fixation of the optical fiber in a launch region serving for determining a starting point for said measure of a distribution of strain of at least part of the optical fiber. Thus, in such embodiments, the clamp mechanism of the first aspect forms part of a launch fixture.

Especially, the elongated device may be a medical device, e.g. in the form of a catheter, a guide wire, an endoscope etc. However, it is to be understood that the invention is applicable also for non-medical use.

In a third aspect, the invention provides a method of clamping an associated optical fiber comprising optical shape sensing properties, the method comprising:
providing a fixing element with at least a portion of its cross section having a circular or elliptical shape which is arranged for engaging with the associated optical fiber,
providing an additional fixing arrangement comprising a straight longitudinal portion arranged for engaging with the associated optical fiber, and
placing the associated optical fiber along said straight longitudinal portion of the additional fixing arrangement,
assembling the fixing element and the additional fixing arrangement, so as to mutually cooperate in fixation of a section of the associated optical fiber in a straight position.

It is appreciated that the same advantages and embodiments of the first aspect apply as well for the second and third aspects. In general the first, second and third aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIGS. 16a and 16b show a sketch and a 3D image of an optical fiber clamp mechanism formed by two rods and 12 spheres (not showing the top clamp for fixing them), FIGS. 17a and 17b show a sketch and a 3D image of an optical fiber clamp mechanism formed by 3 rods (not showing the top clamp for fixing them)

DESCRIPTION OF EMBODIMENTS

Figure 1:
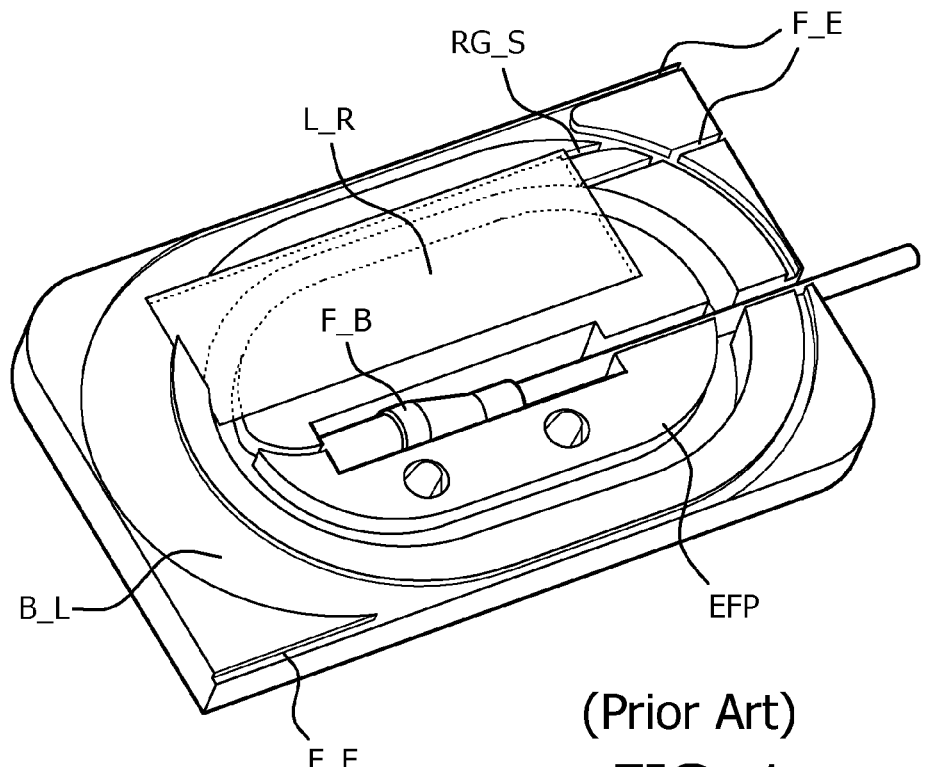
FIG. 1 shows a photo of a prior art launch fixture with a microscope object slide serving as reference for position and orientation of a launch section of an OSS optical fiber.

FIG. 1 illustrates an example of a prior art launch fixture for clamping an optical fiber to fix the fiber properly as well as to keep track of the position and orientation of the starting point for Optical Shape Sensing (OSS). Typically, such launch fixture has a length of 12.5 cm and a width of 7.5 cm. It has a cover to protect the fiber inside and there are possibilities to mount the whole fixture to a table or the like. Further, there may be a buffer loop B_L (e.g. with a curvature radius of about 35 mm) to accommodate for extra length of optical fiber when the connected catheter is bent. A starting point for OSS reconstruction may be created by gluing the launch region L_R of the optical fiber on a microscope object side, or by sliding a few centimeters of straight, tightly fitting capillary over the optical fiber. In the shown example, there is a path for excess fiber EFP, and three fiber exits F_E, as well as a fiber boot F_B. The point RG_S is where the shape of the optical fiber is registered.

Small deviations in angle or straightness may lead to rather large deviations 1 or 2 meters away from the launching region. E.g. a deviation of 10 micron over 2 cm corresponds to a mismatch of 1 mm at 2 meter, which is considered just allowable. This may be achieved with the prior art launch fixture shown FIG. 1, certain ways of gluing induce creep or they are unstable over time, in particular if the device or instrument in which the optical fiber is incorporated is operated, and stresses are transported to the launch fixture.

In case the shape sensing fiber is used for tracking position and shape of a medical instrument, such as a guide wire or a catheter, the fiber is integrated into the instrument. Integration puts boundary conditions on the manufacturability and placement of the launch region. For example, if the ends of the optical fiber are occupied with connectors or medical devices, no capillary can be slid over the fiber anymore. So the launch region has to be defined beforehand.

For optimal flexibility in production and integration one would like to be able to take out the optical fiber, shift the position of the launch region, recalibrate and so on.

From experience it has been shown that if the optical fiber is secured inside a launch fixture by Salol (Phenyl Salicylate; melting point: 41.5° C.; soluble in hot water and acetone), poorly predictable mechanical properties are achieved (changes over time), the fixation is not strong and reliable enough, and it is difficult to glue the optical fiber as a straight section in the launch. In addition, when unbonding the Salol (heating above 41.5° C.), it is possible to damage the acrylate coating often used for coating the optical fiber.

Thus, prior art clamping mechanisms for OSS optical fibers suffer from a number of problems.

Figure 2:
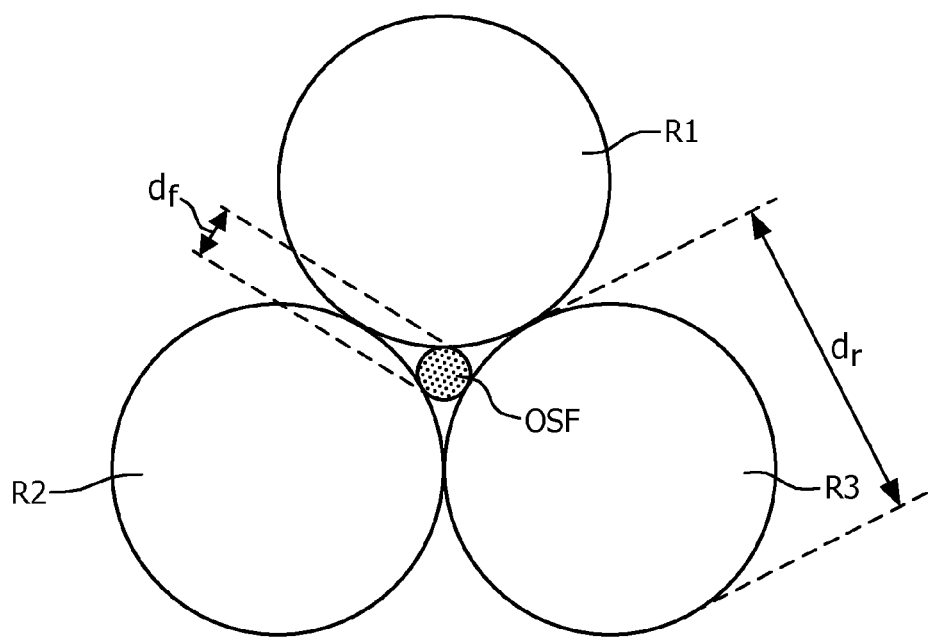
FIG. 2 illustrates a sketch of a cross section of a clamp mechanism embodiment with 3 rods with equal circular diameter matched for fixing an optical fiber.

FIG. 2 shows a cross sectional sketch of a clamping mechanism embodiment according to the invention. In this embodiment, a fixing element is formed by a straight rod R1 with a circular cross section, and an additional fixing arrangement is formed by two straight rods R2, R3 with circular cross sections, e.g. monolithic elements of perfect cylindrical shape. All three rods R1, R2, R3 have similar or equal diameters $d_r$ which is larger than a diameter $d_f$ of the optical fiber OSF which is fixed by all of the three rods R1, R2, R3 cooperating to form a straight longitudinal opening where the optical fiber OSF is arranged. The diameter $d_r$ of the three rods R1, R2, R3 is selected such that the three rods R1, R2, R3 mutually cooperate in fixation of a section of the optical fiber OSF in a straight position. Thus, a combined clamping a straightening effect of the optical fiber is obtained. This is a suitable solution for any clamping of an optical fiber OSDF for OSS, e.g. for registration at any point, or for use as clamping mechanism in a launch fixture. The use of three rods R1, R2, R3 as fixing element and additional fixing arrangement allows easy dismantling of the clamping mechanism since no gluing is involved. Hereby, it can be added at any moment in the integration process of the optical fiber OSF into an instrument, e.g. a medical catheter or guide wire etc.

If follows from simple geometry, that in order to have a precise fit between the rods R1, R2, R3 and the optical fiber OSF, the diameter $d_r$ of the rods is preferably a factor F larger than the diameter $d_f$ of the optical fiber OSF, where:

$$F=\sqrt{3}/(2-\sqrt{3})=3+2\sqrt{3}\approx 6.4641.$$

Thus, with a factor F of more than 6, the rods R1, R2, R3 are relatively large compared to the optical fiber OSF, hence the rods R1, R2, R3 can be made stiff, and they can be handled easily. Preferably, the rods should be straight, stiff and smooth. It may also be preferable to have rods R1, R2, R3 with a selected thermal conductivity. For example, it may be preferred to select rods R1, R2, R3 with low thermal conductivity in order to provide isolation of the launch region from fluctuations in external temperature. On the other hand, thermal conduction to equalize the temperature distribution may be beneficial as well. To prevent build-up of stresses due to thermal expansion of one material with respect to the other. Thermal expansion, or rather, relative thermal expansion can be avoided by using a material with the same thermal expansion coefficient for the rods R1, R2, R3 and the optical fiber OSF. An example of a material for the rods R1, R2, R3 is metal, e.g. steel, however fused silica may also be considered to have advantageous properties.

A feature of the invention is that even if the ends of the optical fiber are occupied with connectors, terminations or medical devices, so that no capillary can be slid over the optical fiber, a mid section can still be fitted with the clamp mechanism according to the invention.

It is to be understood that the principle applies in case the rods do not have circular but rather elliptical cross sections. Circular cross sections may be preferred since they are simpler to manufacture, and they may also be simpler to mount in practical applications. However, elliptical cross sections can in general be used, or cross sections with other shapes, provided they have at least a portion of its circumference serving to engage with the optical fiber which is circular or elliptically shaped. The other part of the circumference may be shaped otherwise, e.g. with flat portions that may facilitate position of a clamp element serving to press the three rods together.

Figure 3A:
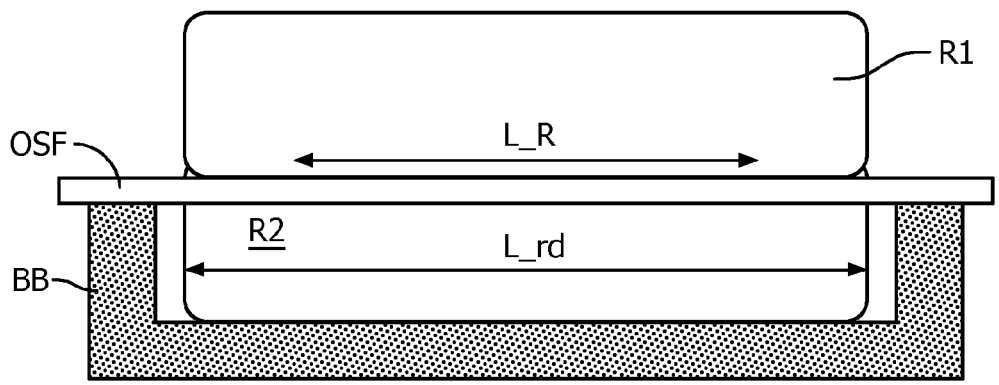
FIGS. 3a and 3b illustrate sketches of two views of a launch fixture embodiment with 3 rods and a base block.
Figure 3B:
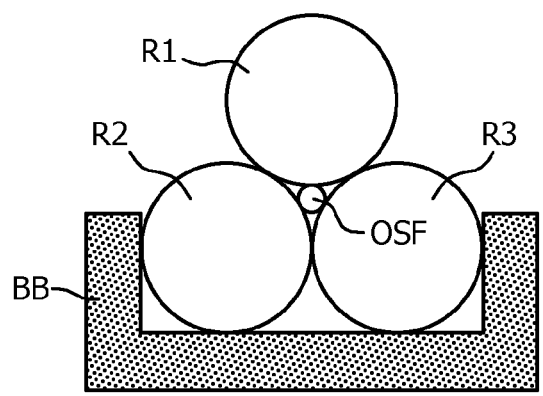
Figure 4A:
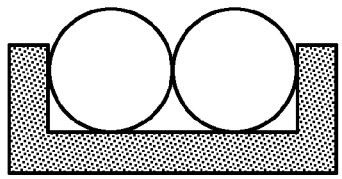
FIG. 4a-4d illustrate sketches of different stages of assembly of a 3 rod embodiment.
Figure 4B:
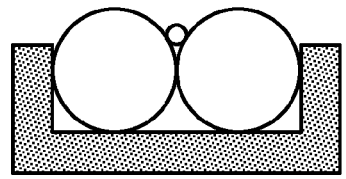
Figure 4C:
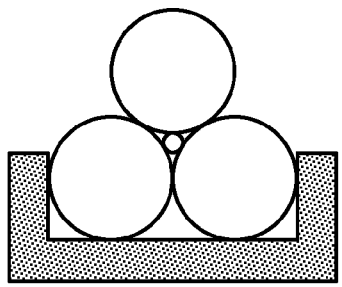
Figure 4D:
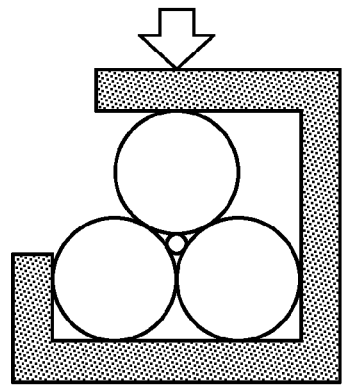

FIGS. 3a and 3b show two orthogonal sectional views of a clamp mechanism embodiment with three rods R1, R2, R3. Here, two nominally sized rods R2, R3 are used as a groove for placing the corresponding diameter of the optical fiber OSF. Then a top rod R1 of a chosen size can be placed over it and pressed down. The two rods R2, R3 are place in a base block BB that has an opening forming a chamber that has a width of twice the diameter of the two rods R2, R3, so as to keep the two rods R2, R3 together. An important insight is that all further pressure is taken by the rods R2, R3 once they are touching, and hence the space available to the optical fiber OSF and the pressure on the optical fiber are clamping force independent. This is particularly true if the optical fiber coating is soft, and if the rods R1, R2, R3 are hard and stiff. A typical coating for optical fibers is polyacrylate which is soft compared to e.g. steel which may be a selected material for forming the rods R1, R2, R3. An added benefit is that the pressure from the rods R1, R2, R3 will straighten the rods, helping to provide a continuum of points of contact along the launch region L_R (e.g. about 20 mm) as opposed to isolated discrete bonding points, such as in prior art bonding methods. This continuum of points creates greater friction between the fiber and the rods and provides greater resistance to rotational and translational forces. In addition, the surface of the rods R1, R2, R3 can be varied to increase or decrease the frictional force on the optical fiber OSF, and may vary depending on the coating of the optical fiber OSF.

In FIG. 3a, a length L_rd of the rods R1, R2, R3 is seen to be longer than the launch region L_R, i.e. the length of the optical fiber OSF that needs to be straight. E.g. the rods may have a length of such as 25-35 mm, e.g. around 30 mm. Further, in FIG. 3a it is seen that the rods R1, R2, R3 have rounded end parts. The rounded end parts serve to prevent pinching of the fiber, especially when combined also with a base block BB which has a chamber which is longer than the length of the rods L_rd.

FIGS. 4a-4d shows cross sectional sketches of an assembly of the clamp mechanism of FIG. 3 in four steps. First, two rods are place in the chamber of the base block, and then the optical fiber is placed in the groove formed by the two rods. Then the top rod is placed to close the opening around the optical fiber. Finally, a clamp is applied to press the top rod against the two lower rods (indicated by the arrow), thus fixing the optical fiber.

Figure 5:
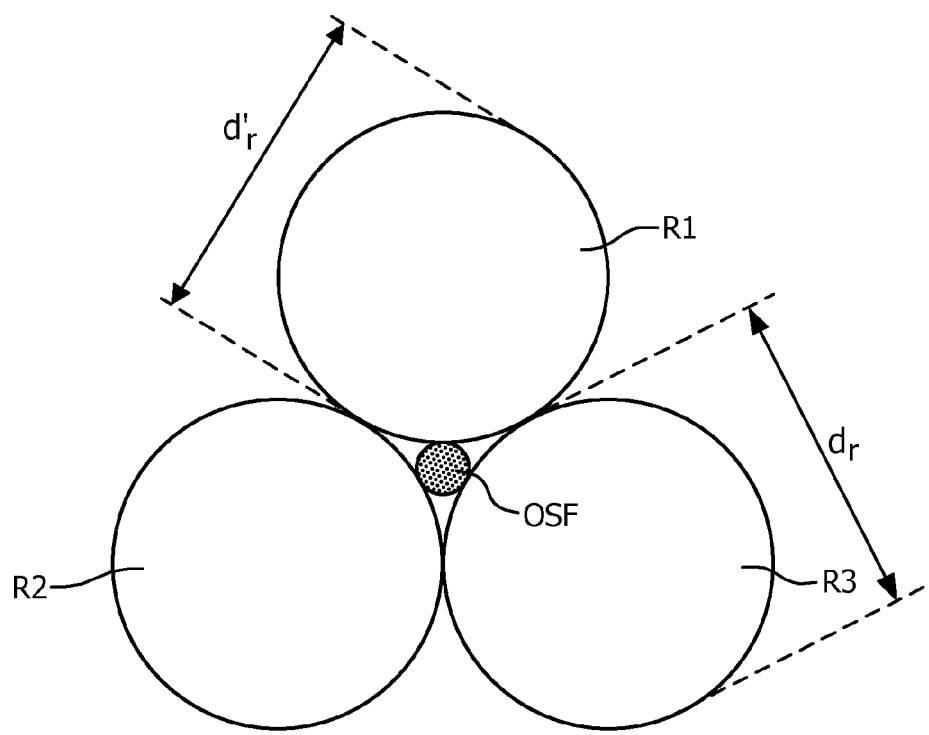
FIG. 5 illustrates a sketch of a cross section of a 3 rod embodiment with one of the rods having a slightly smaller diameter.

FIG. 5 shows a cross sectional sketch of a three rod R1, R2, R3 embodiment where two of the rods R2, R3 have similar or equal diameter $d_r$, while one rod R1 has a slightly different diameter $d'_r$, thus serving to clamp an optical fiber OSF. An insight of the invention is that by tuning the size of only one of the rods R1, it is possible in one case to let the optical fiber slide (a>1), but still to keep it straight, and in another case to clamp it tight enough to keep both its axial and rotational position fixed (a<1). From some simple geometry, and with a=1+ϵ, a ratio between the new and original diameter of the fiber:

$$f=d'_f/d_f=(2\sqrt{(a^2+2a)}-2a-1)/(4a-1)\approx(1+\epsilon/3)/F.$$

When rods of nominal diameter $d_r=Fd_f$ are used, a difference in optical fiber coating diameter of 5 micron would require one of the rods to be 3F×5≈97 micron larger.

$$(d'_r-d_r)/(d'_f-d_f)=\Delta d_r/\Delta d_f \approx 3F \approx 19.4$$

For a practical case, a rod diameter of 1 mm corresponds to a fiber of 154.7 micron which is close to a common value for polyimide coated optical fibers of 125 micron cladding diameter. Other practical cases are for 205 micron and 250 micron cladding where nominal rod diameters of 1.3 mm and 1.6 mm apply.

Thus, some features of 3 rod embodiments can be summed up. Three rods can be used to clamp the optical fiber and keep the optical fiber straight with homogeneous stress. A straight fixation without applying stress (no pressure at all, loose fit) can be obtained. The possibility of separating fixation of the optical fiber and straightening of optical fiber can be provided. The possibility of removing the optical fiber by removing the clamp mechanism, by simply removing (separating) the rods.

Figure 6:
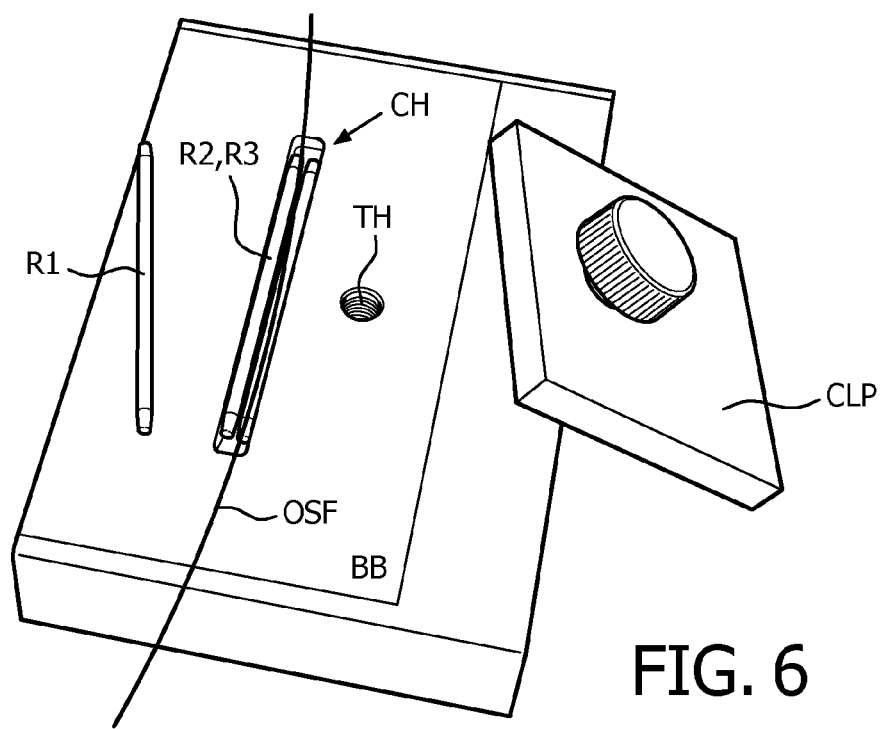
FIG. 6 shows a photo of an optical fiber placed in a launch fixture with 3 rods and a base block with a clamp plate arranged to press the upper rod against the two lower rods.

FIG. 6 shows a photo of an experimental setup of a three rod embodiment. Two parallel rods R2, R3 are glued or clamped together in an opening of a base block BB with a width corresponding to twice a diameter of the two rods R2, R3. Then the optical fiber OSF is put in the resulting groove between the two rods R2, R3, and a third rod R1 is clamped, or even glued, on top of it. In the experimental embodiment, the optical fiber is a 125 micron optical fiber coated with 205 micron acrylic. The ends of the rods are tapered, and the chamber is longer than the rods R2, R3 to prevent pinching of the optical fiber OSF. A thread TH in the base block BB is used for fastening a clamp element to the base block BB with the purpose of applying a pressure to the top rod R1, such that the optical fiber OSF is fixed between the three rods R1, R2, R3.

Figure 7:
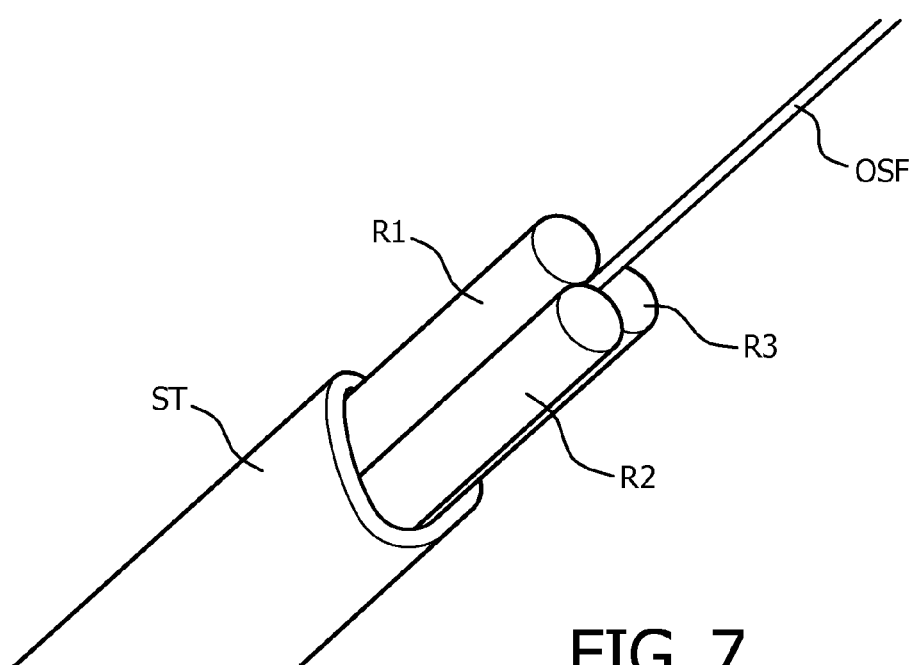
FIG. 7 shows a photo of a 3 rod embodiment, where a shrink tube holds the 3 rods together, thus clamping an optical fiber with a polyimide coating.

FIG. 7 shows a photo of another way of pressing three rods R1, R2, R3 together around an optical fiber OFS, namely by means of shrink tubing. In this example, the optical fiber is coated with polyimide of 154 micron diameter, and the rods R1, R2, R3 have similar diameters of 1 mm.

Various materials may be used for all of the three rod embodiments described above. The rods may be formed by metals, such as steel, e.g. stainless steel, or steel for bearings. The rods may be formed by magnetic materials, in particular the bottom rods could be made ferromagnetic, and the top rod could be a strong magnet, thus no further means for clamping or pressing the rods together may be required. It may also be preferred to form a base block with a ferromagnetic chamber keeping two non-magnetic rods with a strongly magnetized top rod. In the latter case, the bottom rods need not be glued in the chamber of the base block. Still further, one embodiment that has been constructed and tested, has a magnet in the base block together with three ferromagnetic rods, or just one ferromagnetic rod at the top. For Magnetic Resonance Imaging (MRI), non-magnetic metals can be used for the rods, and also for the base block, e.g. aluminium, however ceramics or glass can be used for MRI as well, and these materials can be made to be very hard, smooth and of exact diameter. Using fused silica for the rods, or more precisely, the same material as the optical fiber for OSS is made of, will serve to match axial thermal expansion. The coating should serve as a plastic buffer. Still further, high quality polymers like PEEK (Poly Ether Ether Ketone) can also be used for the rods.

In a special embodiment, a rather soft top rod is used together with two bottom rods defining a straight groove for the optical fiber. The disadvantage is that the pressure may not be reproducible, but it may help in case the optical fiber coating diameter is not well defined, or if it is very thin and hard, such as for polyimide coated fibers. The clamp should provide either constant pressure or define a reproducible space. Alternatively, a soft (compressive) foil may be used between the rods.

Figure 8A:
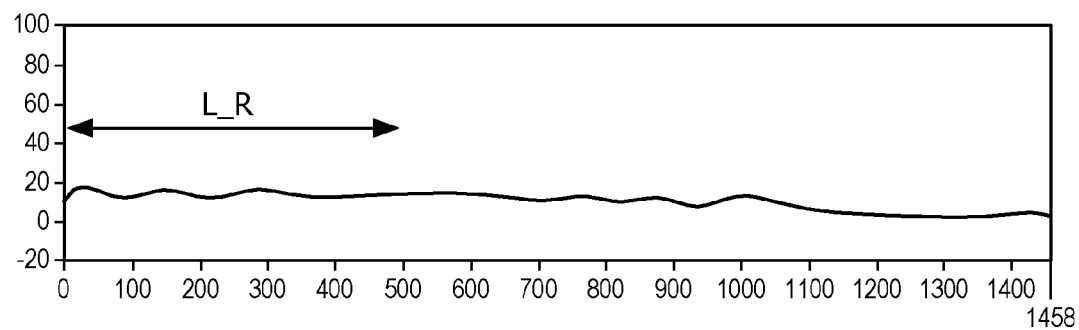
FIGS. 8a and 8b illustrate graphs showing axial strain measured on an optical fiber clamped with a 3 rod embodiment, in FIG. 8a the rods have the same, nominal diameter and the optical fiber fits just right, whereas in FIG. 8b the top rod has a smaller diameter, so that the pressure on the optical fiber is increased.
Figure 8B:
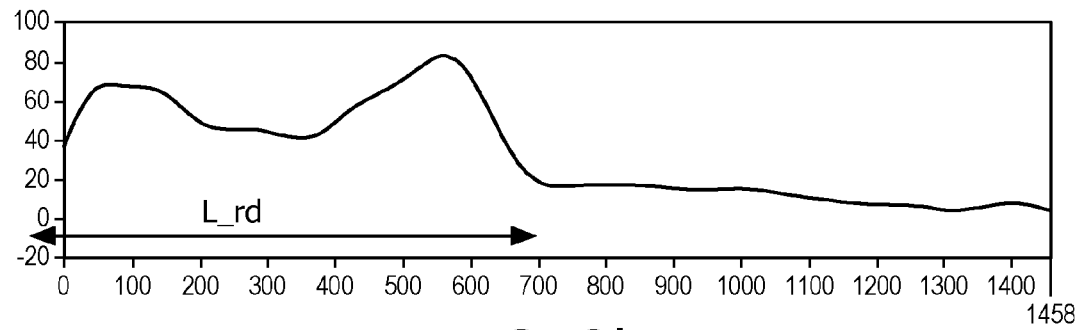

FIGS. 8a and 8b show graphs obtained with the LUNA G3 OSS system to monitor the axial strain on the launch region for two three rod embodiments of the invention. Axial strain on the launch region for a 205 micron coated optical fiber was measured. FIG. 8a shows the first 6 cm in case 3 rods of nominal diameter of 1.3 mm. The optical fiber is nicely clamped and cannot be slid or rotated, but the strain is low and of similar value in and outside the clamped section L_R (20 mm=500 fiber indices). FIG. 8b shows that the axial strain goes up significantly in the clamped section, or at the length of the rods L_rd (30 mm=750 fiber indices), if the top rod is changed to a diameter of only 1.1 mm. However, tests showed that in spite of this increased strain, the reconstructed shape and stability of the shape reconstruction were hardly affected.

The conclusions from the measurements are that straightening the launch part of the optical fiber is very easy with the three rod solution (either with or without fixation). A large multiplication factor (~20) for tolerances on coating diameter is obtained, and it is easily adjusted to an actual size. Still, even of not perfectly matched to the actual size, a good OSS function is obtained with stress on the launch (certainly up to 80 micro strain). In spite of the superior OSS performance, still these three rod embodiments are easy to assemble and disassemble, and thus easy to use for practical application e.g. at a clinic or hospital etc.

Figure 9A:
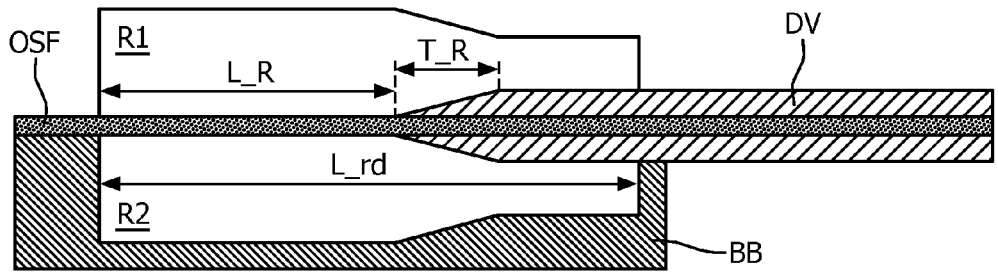
FIGS. 9a and 9b illustrate sketches of two different views of a 3 rod embodiment with an end section where the diameter of the rods is reduced starting by a tapering region.
Figure 9B:
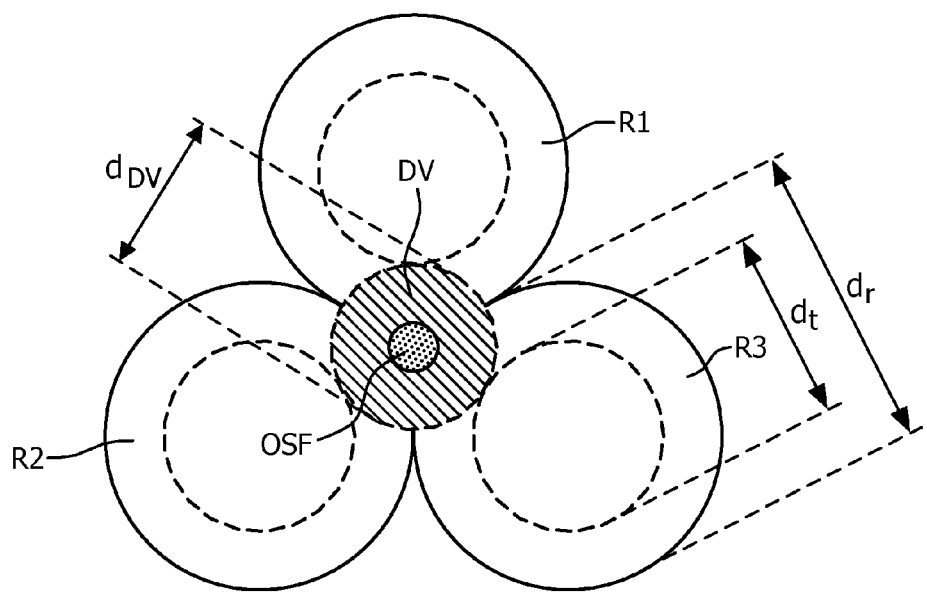

FIGS. 9a and 9b show two different cross sectional views of a three rod embodiment suited for clamping both the optical fiber OSF as well as an instrument or device DV in which the optical fiber OSF is integrated, i.e. a guide wire a catheter or the like, or merely a hollow tube. Managing the transition from the bare OSS optical fiber to an instrument immediately after the launch fixture is challenging. In prior art this is handled by using adhesives such as tape, glue, epoxy, or Cyanoacrylate (Crazy Glue or Loctite), Salol (Phenyl Salicylate), etc. However, these methods require trial-and-error to assemble, i.e. take too much time, and allow effects such as tension, temperature and torsion in the distal instrument or proximal leads to impact the state of the launch section. Low adhesive techniques such as tape tend to degrade over a few days, requiring re-application. High adhesive techniques require permanent attachment of the fiber to a device DV, and it is desirable to re-use the OS In the embodiment shown in FIGS. 9a and 9b, as in the previously described embodiments, two nominally sized rods R2, R3 with diameter $d_r$ can be used as a groove for placing the corresponding diameter of optical fiber OSF. Then a third rod R1 of chosen size can be placed over it and pressed down. The base block BB has a chamber that has a width of twice the diameter of the rods R2, R3 to keep these rods R2, R3 together. In the previous embodiments the three rods have constant diameter throughout their lengths, e.g. except for rounded end parts. In FIGS. 9a and 9b the diameter of the rods R1, R2, R3 decreases towards one end over a tapering region T_R, thus decreasing from one diameter $d_r$ at one end of the tapering region T_R, ending at a smaller diameter $d_t$ at the opposite end of the tapering region T_R. Thus, the longitudinal extension L_rd of the rods R1, R2, R3 has a first part L_R serving as a launch region where the diameter is $d_r$ is selected to be able to clamp the optical fiber OSF, a second part T_R being the tapering region where the diameter gradually decreases to another value $d_t$, and finally a third part with a length of L_rd−(T_R+L_R) with a constant diameter of value $d_t$.

Hereby, a device DV with a normal or tapered tip can be firmly fit, if the diameter $d_t$ is selected to fit a specific size of device DV, such that the diameter $d_{DV}$ of the device DV is clamped in the spaced between the end parts of the three rods R1, R2, R3 with diameter $d_t$. This allows a firm fit of the device DV to the launch region, while ensuring that tension and torque on the device DV is not transmitted to the launch region L_R. In a specific embodiment, the launch region L_R has a length of 15-25 mm, e.g. around 20 mm, while the length of the tapering region T_R is 5-15 mm, e.g. around 10 mm, and the length of the third part of the rods R1, R2, R3 with decreased diameter may be such as 5-20 mm, e.g. 10-15 mm.

Figure 10:
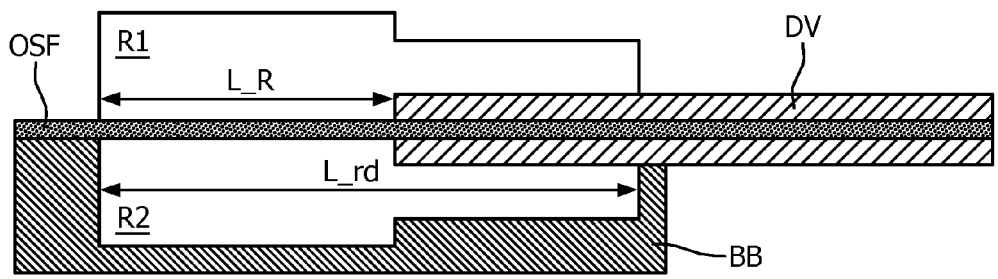
FIG. 10 illustrates a sketch of another 3 rod embodiment with an end section where the diameter of the rods is reduced, but without a tapering region.

FIG. 10 shows a special version of the embodiment of FIGS. 9a and 9b, namely where the tapering region T_R has zero length, and thus in this embodiment the diameter jumps from one value in the launch region L_R to a lower diameter in the end part having a length of (L_rd−L_R). Thereby, an optical fitting to a device DV with a non-tapered tip is provided.

The rods R1, R2, R2 of the embodiments in FIGS. 9 and 10 are still rather easy to manufacture, due to the simple concentric design, and can thus be provided with a high precision in one of the already mentioned materials.

Figure 11:
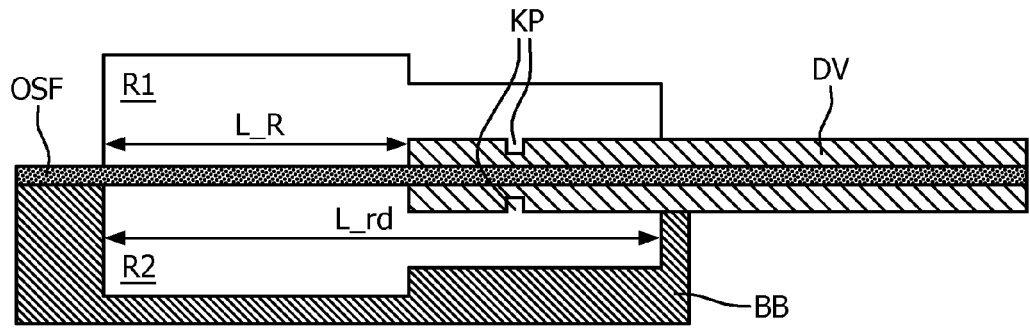
FIGS. 11 and 12 illustrate sketches of two different versions of 3 rod embodiments with keyed interlock to an instrument having an optical fiber incorporated.
Figure 12:
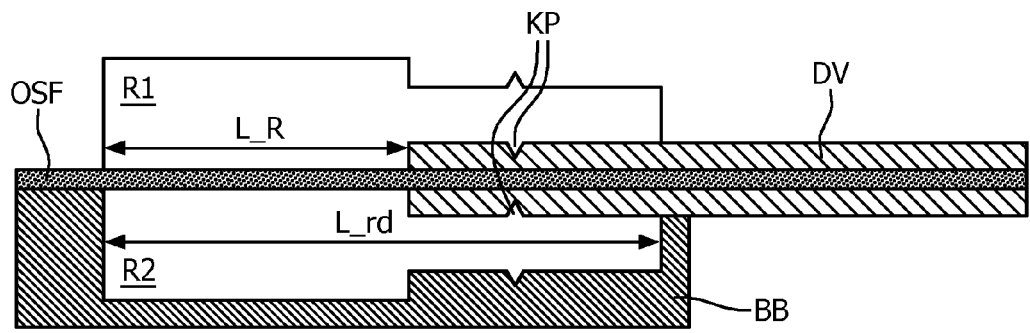

FIGS. 11 and 12 show two embodiments similar to the one in FIG. 10, except for the presence of a keyed portion KP of the three rods R1, R2, R3 positioned on the longitudinal portion of the rods R1, R2, R3 with decreased diameter. However, such keyed portion may also be positioned on the tapered region T_R on the embodiment of FIGS. 9a and 9b. The keyed portion KP serves to provide an interlock mechanism to engage with a corresponding indentation on the device DV in which the optical fiber OSF is integrated. Hereby, it is possible to lock the device DV in fixed position to the launch fixture. FIG. 11 shows a rectangular shaped keyed portion KP, while the keyed portion KP of FIG. 12 has a triangular shape. This can be implemented as a partly cut down portion of the device DV, and a keyed portion of the cylindrical rods R1, R2, R3.

Figure 13:
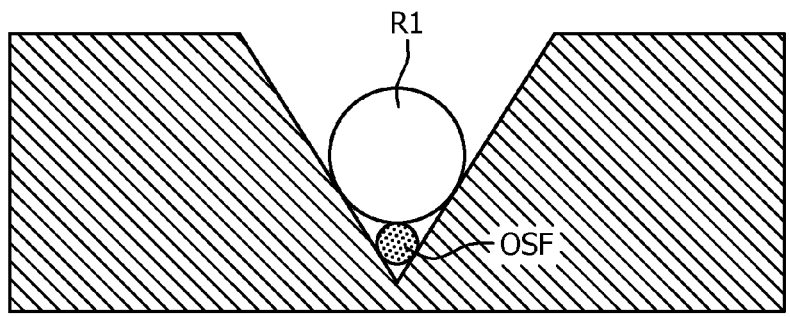
FIG. 13 shows an embodiment where the additional fixing arrangement is constituted by a body with a V-shaped groove, and where the optical fiber is clamped therein by a rod with circular cross section.

FIG. 13 shows a cross sectional sketch of another clamp mechanism embodiment. A body (crossed area) with a straight groove with an opening angle, i.e. a V shaped groove. The straight groove is arranged to accommodate a section of the optical fiber OSF, and to fix the optical fiber OSF in a straight position in cooperation with a fixing element R1, here illustrated as a straight rod with circular cross section. In case the opening angle of the groove is 60°, it can be shown that the diameter of the rod should preferably be 3.0 times the diameter of the optical fiber OSF, in order to be able to fix the optical fiber OSF in the straight position without unnecessary strain. In case the opening angle is different from 60°, it is to be understood that the diameter of the rod R1 should be selected to be different from a factor of 3.0 times the diameter of the optical fiber OSF. This embodiment is based on the same insight, namely that the optical fiber OSF can be clamped in the groove formed by the body, e.g. a monolithic block of metal, instead of the groove shaped opening formed by two adjacent straight rods with circular cross section.

FIGS. 14-16 show illustrations of three different clamp mechanism embodiments where the fixing element comprises a spherical body cooperating with different types of additional fixing arrangements. In FIGS. 14-16, 3D line sketches are shown to the left, while 3D images of the same embodiments are shown to the right.

Figures 14A, 14B:
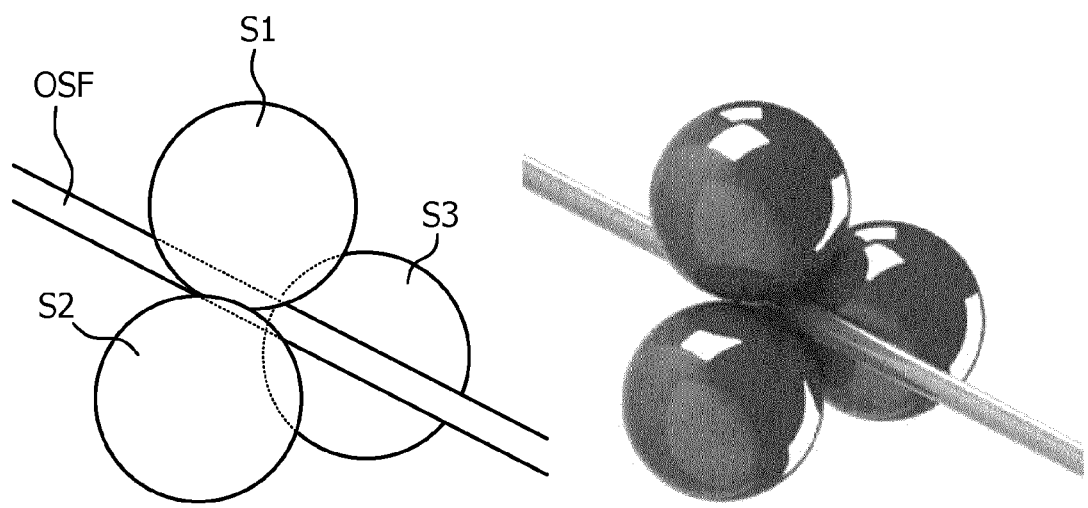
FIGS. 14a and 14b show a sketch and a 3D image of an optical fiber clamp mechanism formed by 3 spheres (not showing the arrangement for fixing the spheres)

FIGS. 14a and 14b show two different illustrations of an embodiment where a point of the optical fiber OSF is fixed by three spheres S1, S2, S3, wherein the diameters of the spheres S1, S2, S3 are selected to match the diameter of the optical fiber OSF, such that they cooperate to fix the optical fiber OFS in one point. Thus, basically this is based on the same insight explained for the three rod embodiments in the foregoing, however using only three spheres S1, S2, S3, it is only possible to fix the optical fiber OFS in one point, not a straight part of the optical fiber OSF. Such embodiment can be used for fixing of a point of an OSS optical fiber OSF, e.g. for registration of a position in space.

However, only if a number of groups of three spheres S1, S2, S3 are placed adjacent to each other, an approximation to fixation along a straight line, or a curved line, can be obtained, and thus such embodiment with a plurality of adjacent sets of three spheres can be suited as a launch fixture.

Figures 15A, 15B:
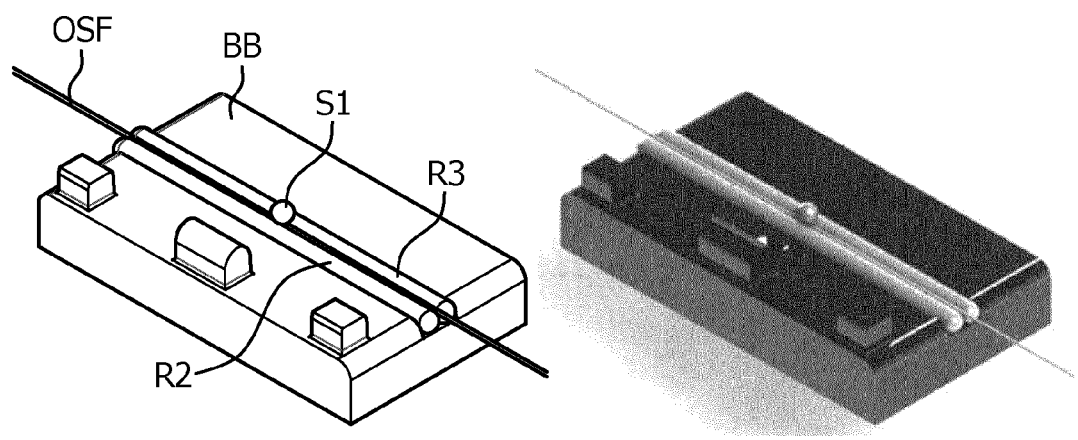
FIGS. 15a and 15b show a sketch and a 3D image of an optical fiber clamp mechanism formed by two rods and a single sphere (not showing the top clamp for fixing them)

FIGS. 15a and 15b show two different illustrations of an embodiment where one single sphere S1 is used as fixing element, and wherein the additional fixing arrangement is constituted by a base block BB with a chamber accommodating two straight rods R2, R3 with circular cross section providing a straight groove for the optical fiber OSF. Thus, basically this is a three rod embodiment, where the upper rod R1 is replaced by a sphere S1 with the same diameter. For some applications, such embodiment may suffice as a launch fixture in spite the fact that the optical fiber OSF is clamped in one point only by the sphere S1.

FIGS. 16a and 16b show two different illustrations of versions of the embodiment of FIG. 15, but where the single sphere S1 is replaced by a plurality of spheres S. 12 spheres S are shown in the illustration as an example. E.g. the spheres S are selected to have the same diameter as the rods R2, R3, or slightly smaller. The plurality of spheres S serve to fix the optical fiber OSF at respective closely spaced points, thus effectively constituting a line fixing of the optical fiber OSF thereby allowing such embodiment to be used as a launch fixture.

It is to be understood that in the embodiment of FIG. 13, the straight rod R1 could in principle be replaced by one or a plurality of spheres to serve as fixing elements instead of the rod R1.

FIGS. 17a and 17b finally show two different illustrations of a three rod embodiment R1, R2, R3, i.e. an embodiment similar to the embodiment of FIG. 16, except that the spheres S are replaced by a straight rod R1 with a circular cross section.

Figure 18:
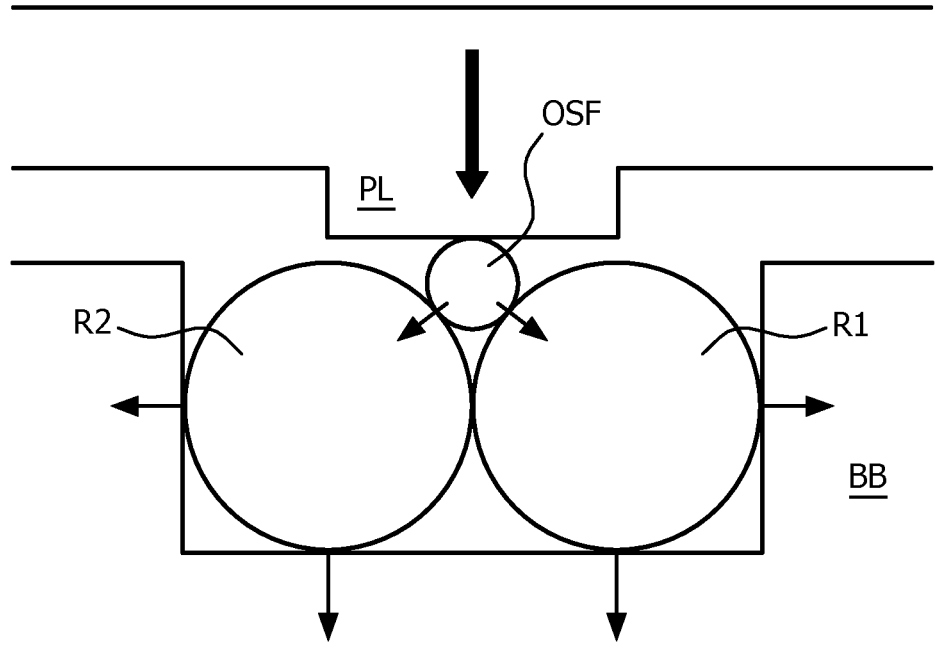
FIG. 18 shows a cross sectional sketch of an embodiment with two circular rods and a plunger with a flat portion pressing the optical fiber against the two rods.

FIG. 18 shows a cross section of a clamp mechanism embodiment, where the fixing element is constituted by a straight rod R1 with a circular cross section. The additional fixing arrangement comprises a second straight rod R2 with a circular cross section, and a base block BB having an opening serving to hold the two rods R1, R2 close together, so as to form a longitudinal groove for an optical fiber OSF. A top surface of the optical fiber OSF stands above a top surface of the two rods R1, R2, creating a small gap. Because of this, when a flat surface plunger PL is pressed down upon it, it presses the optical fiber OSF into the rods R1, R2 with forces distributed evenly on the right rod R2, and the left rod R2, as shown indicated by arrows. Since the rods R1, R2 contact the sides of the opening in the base block BB, at two perpendicular points, these angled forces are resolved to two forces pressing the rods R1, R2 into the opening, and two forces pushing the rods apart. Because the forces are resolved in this way, if the rods R1, R2 were to move apart relative to each other, the optical fiber OSF would sink deeper into the groove between them. As long as the rods R1, R2 do not spread enough for the plunger PL to come in contact with the rods R1, R2, the optical fiber OSF will remain clamped, making this method highly suited to being made with imprecise machining practices and low cost materials.

Figure 19:
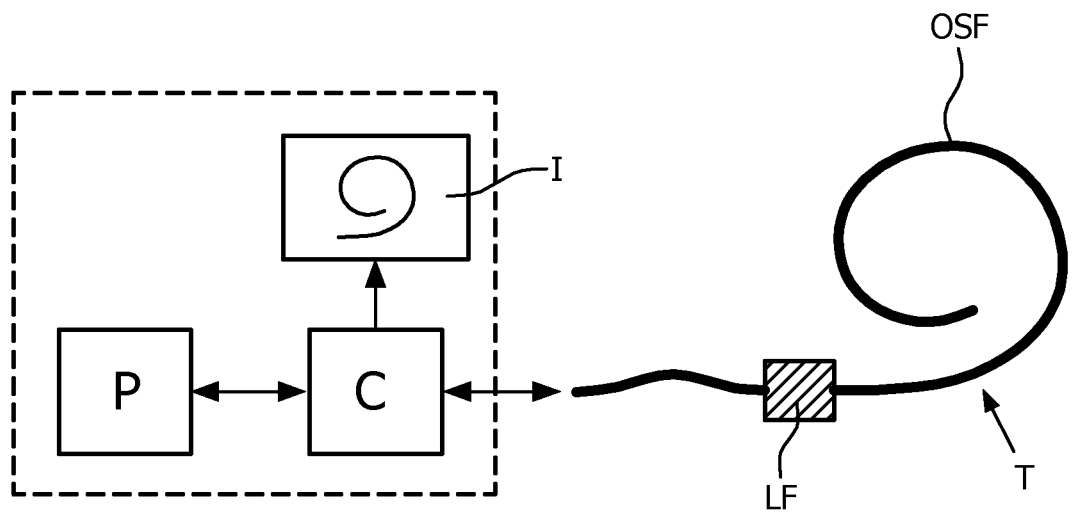
FIG. 19 shows basic elements of an OSS system with a launch fixture according to the invention, and FIG. 20 show steps of a method embodiment.

FIG. 19 illustrates basic parts of an OSS system with an optical fiber OSF with strain sensing optical elements incorporated in an elongated device, e.g. a medical tether T. An optical console C is connected to the optical fiber OSF and arranged to optically interrogate the strain sensing optical therein, and to accordingly determine a measure of a three-dimensional shape of at least a part of the optical fiber OSF and thereby the medical tether T in which the optical fiber OSF is placed. A processor P controls the optical console C, and a 3D image I of the optical fiber OSF can be generated, e.g. displayed as an image on a monitor in real time. The tether T is connected to a launch fixture LF which comprises a clamp mechanism according to the invention, i.e. as described in the foregoing. The launch fixture LF is arranged to serve for determining a starting point for 3D shape reconstruction and thus as a starting point for the 3D image I.

Figure 20:
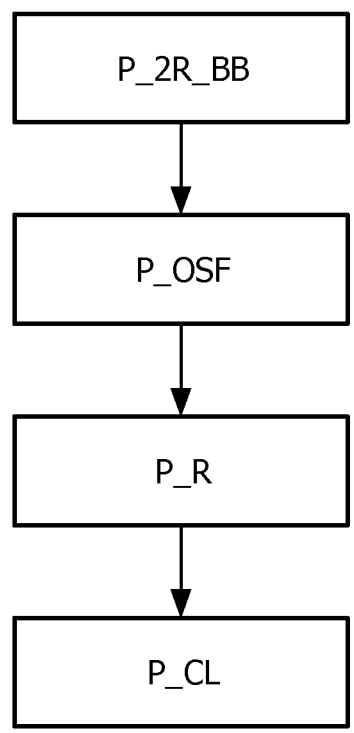

FIG. 20 shows steps of an embodiment of a method of clamping an optical fiber. The method comprises the step P_2R_BB of providing an additional fixing arrangement comprising a base block with an opening in which two straight rods with circular cross sectional area are placed adjacent to each other. Next step comprises providing an optical fiber P_OSF in the straight groove formed by the two adjacent straight rods. Next step comprises providing and placing P_R a fixing element in the form of a straight rod with circular cross section in order to clamp the optical fiber in the longitudinal space between all of the three rods. Finally, the method comprises the step of placing a clamp element to press all of the three rods together, so as to effectively fix the, preferably replaceable, clamp element, e.g. arranged for being mounted on the base block with a thread or other type of fastening or locking mechanism.

In a further method embodiment, the method comprises using the clamp mechanism as a launch fixture for an optical shape sensing device.

To sum up, the invention provides a clamp mechanism for fixation of an optical fiber OSF with optical shape sensing properties arranged for Optical Shape Sensing. A fixing element preferably with a circular cross section serves to engage with the optical fiber OSF, and together with an additional fixing arrangement with a straight longitudinal portion arranged for engaging with the associated optical fiber OSF, a fixation of a section of the optical fiber OSF is provided with the optical fiber OSF in a straight position. In some embodiments, the clamp mechanism can be implemented by three straight rods R1, R2, R3 with circular cross section, e.g. with the same diameter being a factor of such as 6.46 times a diameter of the optical fiber OSF. Hereby an effective fixation and straightening of the optical fiber OSF can be obtained without disturbing strain with a clamp mechanism which is easy to assemble and disassemble in practical applications e.g. when used as a launch fixture, and with the optical fiber OSF incorporated in a medical device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A clamp mechanism arranged for fixation of an associated optical fiber (OSF) wherein the clamp mechanism is configured for being repeatedly assembled and disassembled for removal of the optical fiber, the clamp mechanism comprising:
   an optical fiber (OSF) comprising optical shape sensing properties and having a coating or cover,
   a fixing element comprising a straight rod (R1) with a circular cross section, which is arranged for engaging with the associated optical fiber (OSF),
   an additional fixing arrangement comprising two straight rods (R2, R3) with circular cross sections and a straight longitudinal portion arranged for engaging with the associated optical fiber (OSF),
   wherein the straight rod (R1) of the fixing, element and the two straight rods (R2, R3) of the additional fixing arrangement are made from a material which is hard compared with the soft material of the coating or cover of the optical fiber (OSF), and a base block (BB) with an opening section (CH) arranged for receiving the two straight rods of the additional fixation arrangement and the straight rod of the fixation element, whereby the straight rod of the fixing element (R1) is arranged, together with the two straight rods of the additional fixing arrangement (R2, R3), to form an opening arranged for fixation of a section of the associated optical fiber (OSF) in a straight position.

2. Clamp mechanism according to claim 1, wherein a cross sectional area of the fixing element (R1) in the straight longitudinal portion is larger than a cross sectional area of the associated optical fiber (OSF).

3. Clamp mechanism according to claim 1, wherein the additional fixing arrangement (R2, R3, BB) comprises a base block (BB) with an opening section (CH).

4. Clamp mechanism according to claim 1, wherein the straight rod (R1) of the fixing element, and the two straight rods (R2, R3) of the additional fixing arrangement all have circular cross sections with equal or substantially equal diameters ($d_r$, $d'_r$).

5. Clamp mechanism according to claim 4, wherein at least one of: the straight rod (R1) of the fixing element, and one of the two straight rods (R2, R3) of the additional fixing arrangement, has a rounded end portion.

6. Clamp mechanism according to claim 1, wherein at least a part of the fixing element (R2) and a part of the additional fixing arrangement (R2, R3, BB) have magnetic properties, so as to magnetically attract each other in an assembled state of the clamp mechanism.

7. Clamp mechanism according to claim 1, wherein an end portion of the fixing element (R1), and an end portion of the additional fixing arrangement (R2, R3), are shaped for holding an end portion of an associated device (DV) in which the associated optical fiber (OSF) is incorporated.

8. An optical shape sensing system comprising:
   an elongated device (DV) comprising an optical fiber (OSF) comprising optical shape sensing properties and having a coating or cover,
   a clamp mechanism arranged for fixation of the optical fiber (OSF) and configured for being repeatedly assembled and disassembled for removal of the optical fiber, the clamp mechanism comprising a fixing element (R1) comprising a straight rod (R1) with a circular cross section, which is arranged for engaging with the optical fiber (OSF), and an additional fixing arrangement comprising two straight rods (R2, R3) with circular cross sections and a straight longitudinal portion arranged for engaging with the associated optical fiber (OSF), —wherein the straight rod (R1) of the fixing element and the two straight rods (R2, R3) of the additional fixing arrangement are made from material which is hard compared with the soft material of the coating or cover of the optical fiber (OSF), and a base block (BB) with an opening section (CH) arranged for receiving the two straight rods of the additional fixation arrangement and the straight rod of the fixation element, whereby the straight rod of the fixing element (R1) is arranged, together with the two straight rods of the additional fixing arrangement (R2, R3), to form an opening arranged for fixation of a section of the associated optical fiber (OSF) in a straight position, and
   an optical console system (P, C) arranged for interrogating the optical fiber (OSF), and to accordingly determine a measure of a three-dimensional shape (I) of at least a part of the optical fiber (OSF).

9. System according to claim 8, wherein the clamp mechanism is arranged for fixation of the optical fiber (OSF) in a launch region (L_R) serving for determining a starting point for said measure of a three-dimensional shape (I) of at least part of the optical fiber (OSF).

10. Method of clamping an associated optical fiber (OSF) comprising optical shape sensing properties, the method comprising:
   providing a fixing element (P_R) with at least a portion of its cross section having a circular or elliptical shape which is arranged for engaging with the associated optical fiber,
   providing an additional fixing arrangement (P_2B_BB) comprising a straight longitudinal portion arranged for engaging with the associated optical fiber,
   wherein the straight rod (R1) of the fixing element and the two straight rods (R2, R3) of the additional fixing arrangement are made from a material which is hard compared with the soft material of the coating or cover of the optical fiber (OSF),
   placing the associated optical fiber (P_OSF) along said straight longitudinal portion of the additional fixing arrangement,
   assembling the fixing element and the additional fixing arrangement (P_CL), so as to mutually cooperate in fixation of a section of the associated optical fiber in a straight position.

* * * * *